(12) United States Patent
Duffield

(10) Patent No.: US 6,886,612 B2
(45) Date of Patent: May 3, 2005

(54) METHOD AND APPARATUS FOR TRANSFERRING A DEFINED QUANTITY OF POWDER

(75) Inventor: Howard Peter Duffield, Ware (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/276,762
(22) PCT Filed: May 31, 2001
(86) PCT No.: PCT/EP01/06196
§ 371 (c)(1), (2), (4) Date: Nov. 19, 2002
(87) PCT Pub. No.: WO01/96181
PCT Pub. Date: Dec. 20, 2001

(65) Prior Publication Data
US 2003/0131905 A1 Jul. 17, 2003

(30) Foreign Application Priority Data
Jun. 10, 2000 (GB) .............................. 0014082

(51) Int. Cl.[7] ................................................. B05B 1/20
(52) U.S. Cl. ........................... 141/284; 141/12; 141/71; 141/73
(58) Field of Search ............................ 141/12, 71–81, 141/248; 73/864.44, 864.45; 53/464.44, 464.45

(56) References Cited

U.S. PATENT DOCUMENTS

| 3,656,518 | A | | 4/1972 | Aronson |
| 3,847,191 | A | * | 11/1974 | Aronson ....................... 141/12 |
| 4,116,247 | A | * | 9/1978 | Zanasi ......................... 141/392 |
| 4,341,244 | A | | 7/1982 | Facchini |
| 4,850,259 | A | * | 7/1989 | Morris ........................... 86/31 |

* cited by examiner

*Primary Examiner*—Gene Mancene
*Assistant Examiner*—Peter deVore
(74) *Attorney, Agent, or Firm*—James P. Riek

(57) ABSTRACT

There is provided a method of transferring a defined quantity of powder comprising compacting a target area of powder; dipping a tube into the compacted target area of powder to fill the tube with a defined volume of powder; and transferring the defined volume of powder from the tube.

67 Claims, 9 Drawing Sheets

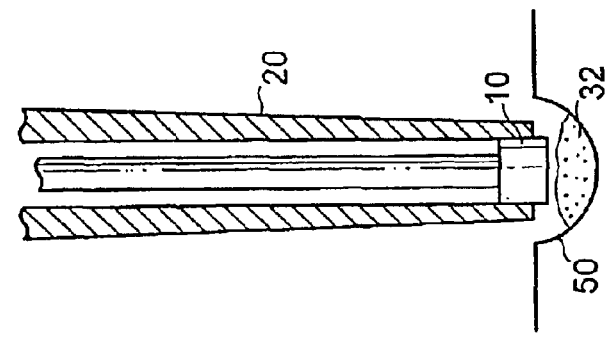
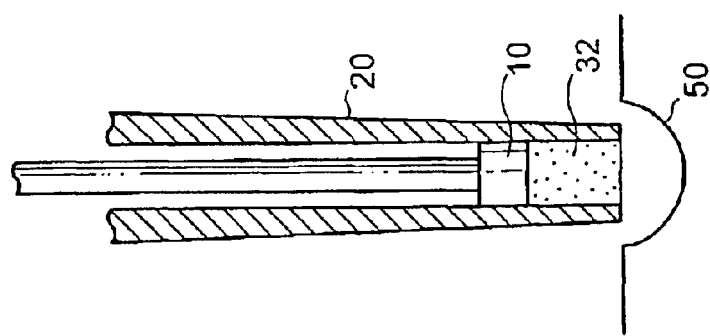
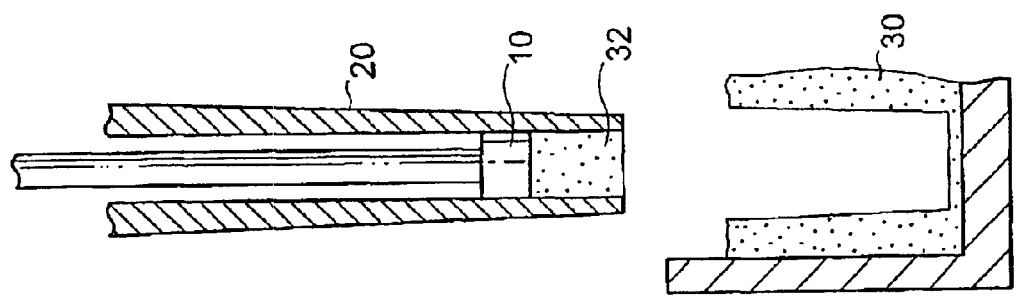

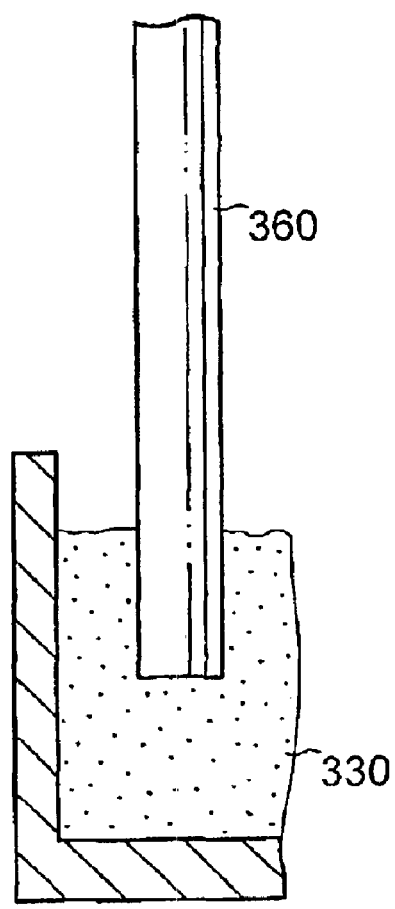
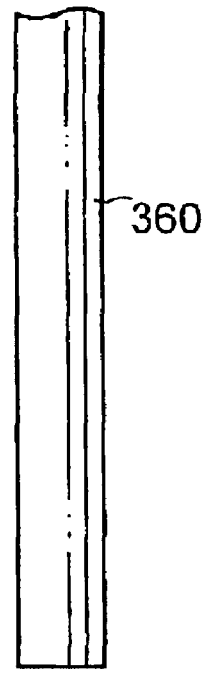
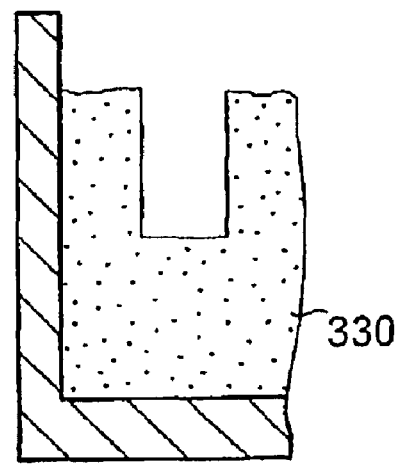
FIG. 4A   FIG. 4B

METHOD AND APPARATUS FOR TRANSFERRING A DEFINED QUANTITY OF POWDER

This application is filed pursuant to 35 USC 371 as a United States National Phase Application of International Patent Application Ser. No. PCT/EP01/06196 filed 31 May 2001, which claims priority from GB 0014082.2 filed on Jun. 10, 2000 in the United Kingdom.

FIELD OF INVENTION

This invention relates to a method and apparatus for transferring a defined quantity of pre-compacted powder. This invention has particular application to transferring a defined quantity of powdered medicament into a pack, for example a blister pack, for use in a drug delivery system such as an inhalation device.

BACKGROUND TO THE INVENTION

The use of dosating apparatus to measure and transfer a defined volume of powder is well known. Typically the dosating apparatus comprises a dosator piston located in a sleeve, the dosator piston being retractable within the sleeve to create a cavity. The dosating apparatus is lowered into a powder reservoir to collect a sample of powder in the cavity and the powder is then ejected from the cavity into a suitable container.

Some of the problems involved in such a process concern optimisation of the fill accuracy and reproducibility, and reducing the aeration of the powder. Improvements to the dosating process made by prior art systems have typically involved either compacting the powder contained in the cavity or ensuring that air does not enter the cavity when filling. Compacting the powder when in the sleeve only compacts and reduces in size the sample already removed, improving packing but not the actual accuracy of the dose. Ensuring that air does not enter the cavity as the apparatus is lowered into the powder by retracting the dosator piston as the apparatus moves through the powder bed improves the filling to a certain extent but the density of the powder in the bed is not altered. A vacuum in the bottom of a powder reservoir may be used to improve the uniformity of the density of the bed. However, when the powder comprises a medicament and an excipient, the medicament particles are stripped from the excipient by the vacuum and a filter is required to capture the medicament particles.

The Applicants have found that the dose to dose repeatability and accuracy of the filling process can be improved by compacting the powder in the reservoir prior to removing the dose of powder to improve the uniformity of the density of the bed and to remove air from the bed. Compacting the powder in the bed prior to removing a sample has the advantage that the powder under the target is free to move within and away from the target area if necessary, leading to production of a bed with a more uniform density to ensure that all samples removed are of equal size.

The whole bed may be compacted prior to removal of the sample powder or alternatively small local areas of the bed may be compacted, corresponding to the area which will be removed. Compacting local areas of the bed has the advantage that the bed is easier to disrupt and prepare for the next round of sampling.

SUMMARY OF THE INVENTION

According to the invention there is provided a method of transferring a defined quantity of powder comprising:
a) compacting a target area of powder;
b) dipping a tube into said compacted target area of powder to fill said tube with a defined volume of powder; and
c) transferring said defined volume of powder from said tube.

Preferably the powder is compactable to between 10 and 99% of its original density. More preferably the powder is compactable to between 20 and 50% of its original density.

In one aspect of the invention the compaction is achievable by the use of a compaction pin.

In another aspect the compaction is achievable by the use of a compaction plate. The plate may compact the target area of powder or may compact the whole powder bed.

In a further aspect the compaction is achievable by the use of a dosator piston located within the tube such that it protrudes from the dipping end of the tube.

In a further aspect the compaction is achievable by the use of a dosator piston located within the tube such that it is essentially flush with the dipping end of the tube. By essentially flush it is meant that the dosator piston is preferably flush with the dipping end of the tube, however small variations in the position of the dosator piston with respect to the dipping end of the tube may be envisaged.

Preferably said dosator piston is slidably retractable within the tube following compaction to create a cavity for filling with the defined volume of powder. The dosator piston is retractable by a pre-determined distance to allow for precise metering of compacted powder.

Preferably the tube is tapered towards its dipping end.

Preferably the target area of powder is greater than the inner cross sectional area of the tube. Alternatively the target area of powder is equal to the inner cross sectional area of the tube.

The invention further comprises compacting the powder in the tube subsequent to filling the tube with the defined quantity or volume of powder. The dosator piston is initially retracted within the tube to create a larger cavity than usually required. After filling the cavity is then reduced in size to compact the powder within the tube. This extra step may have an advantage when a small container is required to be filled with an increased amount of powder.

Preferably the defined volume of powder is transferable from the tube by slidable movement of the dosator piston to eject the powder. The dosator piston is moved within the tube to reduce the size of the cavity until the dosator piston is at least flush with the dipping end of the tube or protruding.

Preferably the method additionally comprises transferring the powder to a container. Preferably the container is selected from the group consisting of a blister pocket, an injection moulded plastic pocket and a capsule. The filled tube is raised out of the powder bed and aligned with the container before the powder is ejected.

An additional component of the invention comprises applying a seal to each end of the filled tube, subsequent to dipping the tube into the compacted target area of powder.

A further additional component of the invention comprises placing said sealed tube in a drug delivery system. Suitable drug delivery systems include inhalation devices used to deliver powdered medicament.

A further additional component of the invention comprises piercing said seal immediately prior to transferring the defined volume of powder.

Preferably the piercing is achievable by the use of a piercing pin.

Preferably said piercing pin forms an integral part of said drug delivery system.

Preferably the defined volume of powder is transferable from said tube by use of a transferring pin to eject the powder into the drug delivery system. The powder is then ready for immediate inhalation by the patient and the empty tube may be disposed of.

Preferably said transferring pin forms an integral part of the drug delivery system.

Preferably the piercing pin and the transferring pin are identical.

An additional component of the invention comprises levelling the powder prior to compaction.

Preferably the levelling is achieved by the use of a leveller blade movable on a linear sweeping path.

In one aspect said leveller blade is perpendicular to said linear sweeping path.

In another aspect the leveller blade presents a forward acute angle to the linear sweeping path. That is to say, the angle between the direction of the sweeping path and the blade is less than 90°. Preferably the forward acute angle is between 1 and 60°. More preferably the forward acute angle is between 40 and 50°.

Alternatively, a curved or articulated blade or a blade presenting an obtuse angle to the linear path may be used to level the powder. Optionally the blade may be passed through the powder bed more than once. The number of passes of the blade through the bed can be varied according to the properties of the powder. Alternatively multiple blades may be used to level the powder.

An additional component of the invention comprises disrupting the powder following removal of the defined quantity or volume of powder.

Preferably the powder comprises a medicament. Preferably the medicament is selected from the group consisting of albuterol, salmeterol, fluticasone propionate and beclomethasone dipropionate and salts or solvates thereof and any mixtures thereof. Preferably said mixture comprises a combination of salmeterol xinafoate and fluticasone propionate.

Preferably the powder further comprises an excipient. Preferably the excipient is a sugar. A suitable sugar comprises lactose.

Alternatively the powder is selected from the group consisting of explosive powder, powdered sweeteners, powdered herbal products, powdered food supplements and vitamins. The explosive powders are suitable for use in munitions or in pyrotechnics.

According to the invention there is also provided an apparatus for transferring a defined quantity of powder which comprises;
a) a powder reservoir;
b) a compactor for compacting a target area of powder;
c) a tube suitable for containing a defined volume of powder; and
d) a transferor to transfer said defined volume of powder from said tube.

By powder reservoir it is meant a container suitable for containing powder.

In one aspect of the invention the compactor comprises a compaction pin.

In another aspect the compactor comprises a compaction plate.

In a further aspect the compactor comprises a dosator piston located within the tube such that it protrudes from the dipping end.

In an alternative aspect the compactor comprises a dosator piston located within the tube such that it is essentially flush with the dipping end. By essentially flush it is meant that the dosator piston is preferably flush with the dipping end of the tube, however small variations in the position of the dosator piston with respect to the dipping end of the tube may be envisaged.

Preferably said dosator piston is slidably retractable within the tube to create a cavity for filling with the defined volume of powder. The dosator piston is retractable by a pre-determined distance to allow for precise metering of compacted powder.

Preferably the tube is tapered towards its dipping end.

Preferably the target area of powder is greater than the inner cross sectional area of the tube. Alternatively the target area of powder is equal to the inner cross sectional area of the tube.

An additional component of the invention comprises a seal applier to apply a seal to each end of the filled tube, subsequent to dipping the tube into the compacted target area of powder.

A further additional component of the invention comprises a loader to load drug delivery system with said sealed tube. Suitable drug delivery systems include inhalation devices used to deliver powdered medicaments.

A further additional component of the invention comprises a piercer to pierce said seal immediately prior to transferring the defined volume of powder.

Preferably the piercer comprises a piercing pin. Preferably said piercing pin forms an integral part of said drug delivery system.

Preferably the transferor comprises a transferring pin. The transferring pin is inserted into the tube to eject the powder into the drug delivery system. The powder is then ready for immediate inhalation by the patient and the empty tube may be disposed of.

Preferably said transferring pin forms an integral part of the drug delivery system.

Preferably the transferring pin and piercer pin are identical.

In one aspect of the invention the transferor transfers the defined volume of powder to a container. Preferably the container is selected from the group consisting of a blister pocket, an injection moulded plastic pocket and a capsule. The filled tube is raised out of the powder bed and aligned with the container before the powder is transferred. Preferably the transferor comprises the dosator piston which slidably moves within the tube to eject the powder. The dosator piston is slidably moved until it is at least flush with the dipping end of the tube or protruding from it.

An additional component of the invention comprises a leveller to level the powder prior to compaction.

Preferably the levelling is achieved by the use of a leveller blade movable on a linear sweeping path.

Preferably said leveller blade is perpendicular to said linear sweeping path.

Alternatively the leveller blade presents a forward acute angle to the linear sweeping path. That is to say, the angle between the direction of the sweeping path and the blade is less than 90°. Preferably the forward acute angle is between 1 and 60°. More preferably the forward acute angle is between 40 and 50°.

Alternatively, a curved or articulated blade or a blade presenting an obtuse angle to the linear path may be used to level the powder. Optionally the blade may be passed through the powder bed more than once. The number of passes of the blade through the bed can be varied according to the properties of the powder. Alternatively multiple blades may be used to level the powder.

An additional component of the invention comprises a disrupter to disrupt the powder following removal of the defined quantity of powder.

Preferably the powder comprises a medicament. Preferably the medicament is selected from the group consisting of albuterol, salmeterol, fluticasone propionate and beclomethasone dipropionate and salts or solvates thereof and any mixtures thereof. Preferably said mixture comprises a combination of salmeterol xinafoate and fluticasone propionate.

Preferably the powder further comprises an excipient. Preferably the excipient is a sugar. A suitable sugar comprises lactose.

Alternatively the powder is selected from the group consisting of explosive powder, powdered sweeteners, powdered herbal products, powdered food supplements and vitamins. The explosive powders are suitable for use in munitions or in pyrotechnics.

The invention also provides a transferred powder sample obtainable by the method as herein described.

BRIEF DESCRIPTION OF THE DRAWINGS

The invention will now be described with reference to the accompanying drawings in which:

FIGS. 1e, 1f and 1g show the powder transfer stages subsequent to the filling stage shown in FIGS. 1c and 1d;

FIGS. 4a and 4b show an alternative compaction stage to that shown in FIGS. 1a and 1b in accord with the present invention;

DETAILED DESCRIPTION OF THE DRAWINGS

Figure 1A:
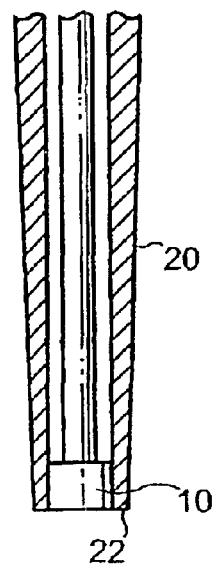
FIGS. 1a and 1b show compaction stages in accord with the present invention.
Figure 1B:
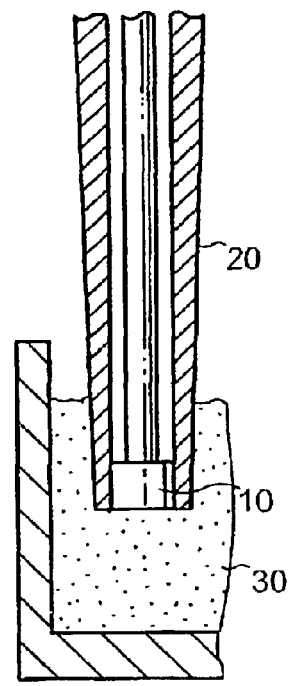
Figure 1C:
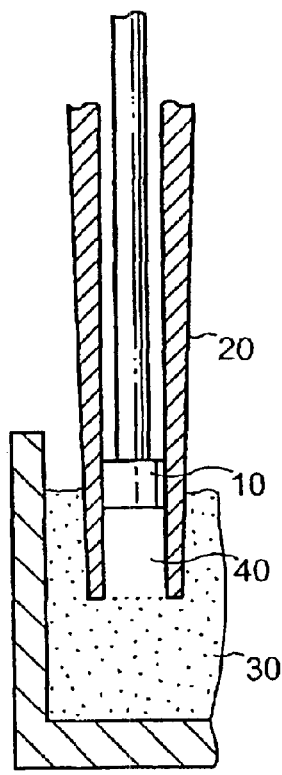
FIGS. 1c and 1d show filling stages subsequent to the compaction stages in FIGS. 1a and 1b in accord with the present invention.
Figure 1D:
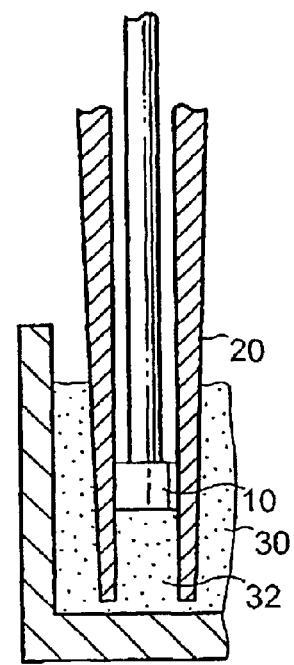

FIGS. 1a to 1g show a complete cycle for transferring a defined quantity of powder comprising compaction, filling and transfer. Dosator piston 10 is located in sleeve 20 such that the dosator piston 10 is flush with the dipping end 22 of the sleeve 20 (FIG. 1a). The sleeve 20 and its internal bore may be of any shape in cross-section (e.g. circular, square, rectangular, hexagonal) provided the bore and piston are of the same cross-sectional shape and that the piston 10 fits snugly within and against the walls of the bore. The dosator piston 10 and sleeve 20 are lowered into the reservoir of powder 30 and the dosator piston 10 compacts the area of powder 30 that it contacts (FIG. 1b). Dosator piston 10 is retracted up the sleeve 20 to create a cavity 40 (FIG. 1c). The dosator piston 10 and sleeve 20 are then moved down through the compacted powder 30 to force a defined quantity or volume (or dose) 32 of the compacted powder 30 into the cavity 40 (FIG. 1d). Dosator piston 10, sleeve 20 and the defined volume 32 of compacted powder 30 in the cavity 40 are then raised out of the reservoir of powder 30 (FIG. 1e) and brought into registration with a container 50, for example a blister pocket of a blister pack (FIG. 1f). Finally, dosator piston 10 is moved towards the dipping end 22 of the sleeve 20 to eject the defined quantity or volume 32 of powder 30 from the cavity 40 (FIG. 1g) into the blister pocket 50.

It will be understood that a number of means can be utilised to remove excess powder from the external edges of the dipping end 22 of the sleeve 20 once cavity 40 has been filled with powder 30. These include the use of stripper wire(s) (not shown) or blade(s) (not shown) which may be suspended above the reservoir of powder 30 and wiped against the external edges of the dipping end 22 by movement of the wire or blade across the edge. An alternative method involves rotating the dipping end 22 of the sleeve 20 relative to the reservoir of powder 30 when the dipping end 22 is immersed in the reservoir.

Figure 2A:
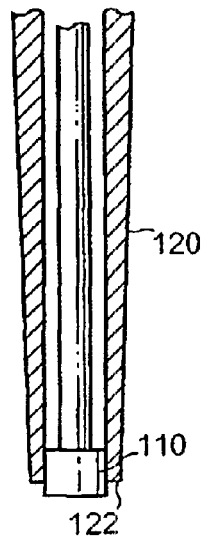
FIGS. 2a and 2b show an alternative compaction stage to FIGS. 1a and 1b in accord with the present invention.
Figure 2B:
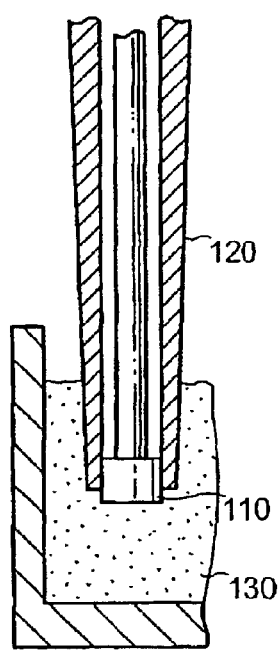

FIGS. 2a and 2b show an alternative compaction stage to that shown in FIGS. 1a and 1b. Dosator piston 110 is located in sleeve 120 such that the dosator piston 110 protrudes from the dipping end 122 of the sleeve 120 (FIG. 2a). The dosator piston 110 and sleeve 120 are lowered into the reservoir of powder 130 and the dosator piston 110 compacts the area of powder 130 that it contacts (FIG. 2b).

Figure 3A:
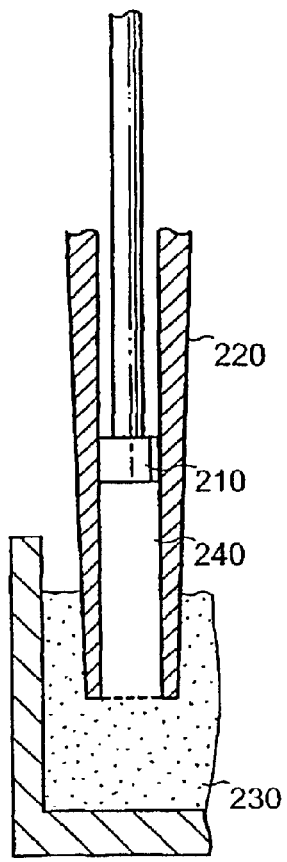
FIGS. 3a, 3b and 3c show an alternative filling stage to FIGS. 1c and 1d in accord with the present invention.
Figure 3B:
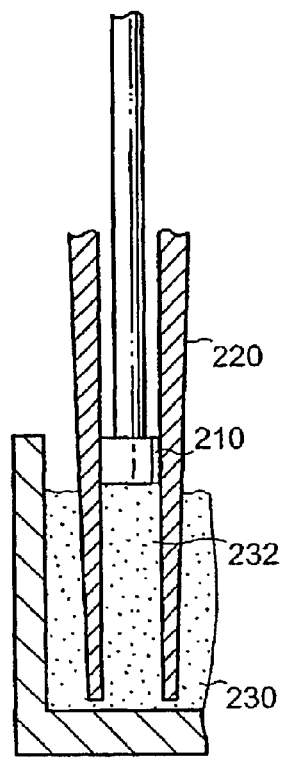
Figure 3C:
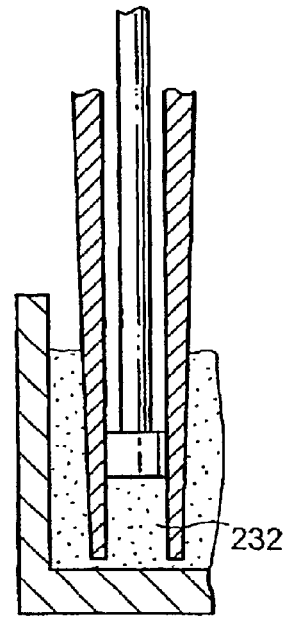

FIGS. 3a, 3b and 3c show an alternative filling stage to FIGS. 1c and 1d. Dosator piston 210 is retracted up the sleeve 220 following compaction of the powder, to create a cavity 240 (FIG. 3a). The cavity 240 is larger than that of the cavity 40 in FIG. 1c. The dosator piston 210 and sleeve 220 are then moved down through the compacted powder 230 to force the powder into the cavity 240 (FIG. 3b). Dosator piston 210 is then moved relative to the sleeve 220 to reduce the size of the cavity 240 (FIG. 3c). This has the effect of further compacting the defined quantity or volume 232 of powder 230 in the cavity 240. The process then continues with transfer steps as shown in FIGS. 1e, 1f and 1g.

It will be understood that an alternative form of filling cavity 240 with powder 230 involves lowering the dipping end 222 of the sleeve 220 into the reservoir of powder 230 and pushing powder 230 into the cavity 240 from below (not shown). Compaction pins (not shown) positioned at the base of the reservoir of powder 230, and below the sleeve 220, could push powder 230 into cavity 240.

FIGS. 4a and 4b show an alternative compaction process to that shown in FIGS. 1a and 1b or 2a and 2b. A compaction pin 360 is lowered into the reservoir of powder 330 to compact the area of powder 330 that it contacts (FIG. 4a). The compaction pin 360 is then raised out of the powder 330 and the process can then continue using a dosator piston 310 in a sleeve 320 as shown in FIGS. 1c to 1g.

Figure 5A:
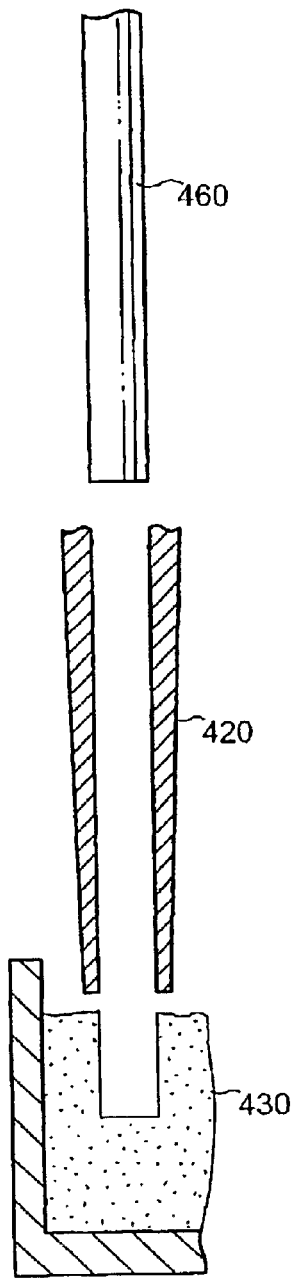
FIGS. 5a, 5b and 5c show a filling stage subsequent to FIGS. 4a and 4b or alternative to that shown in FIGS. 1c and 1d or in FIGS. 3a, 3b and 3c in accord with the present invention.
Figure 5B:
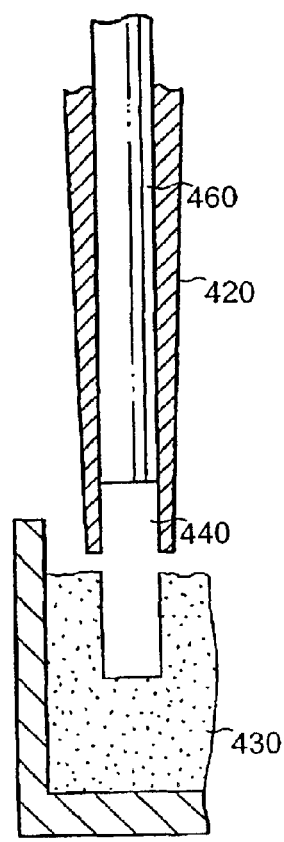
Figure 5C:
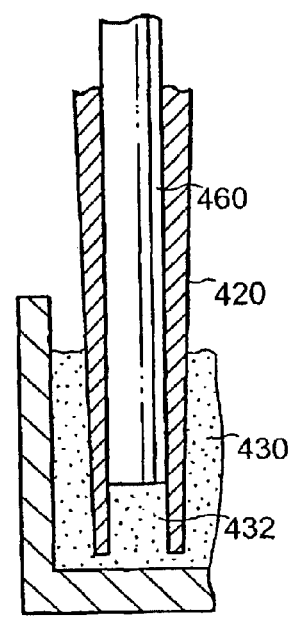

FIGS. 5a, 5b and 5c show an alternative to the process shown in FIGS. 1c to 1e. The compaction pin 460 is lowered into the sleeve 420 to create a cavity 440 for filling with a defined volume of powder 430 (FIGS. 5a and 5b). The compaction pin 460 and sleeve 420 are then lowered into the reservoir of powder 430 to fill the cavity 440 with compacted powder 430 (FIG. 5c). The process can then continue by removing the compaction pin 460 and sleeve 420 from the reservoir of powder 430 and using the compaction pin 460 to eject the powder 432 from the cavity 440 into a container (not shown) as shown in FIGS. 1e to 1g for a dosator piston.

It should be appreciated that the dosator pistons, compaction pins and sleeves shown in the above figures may form part of a multi-dosing system with multiples of these apparatus components all operating simultaneously to remove defined quantities of powder for transfer.

Figure 6A:
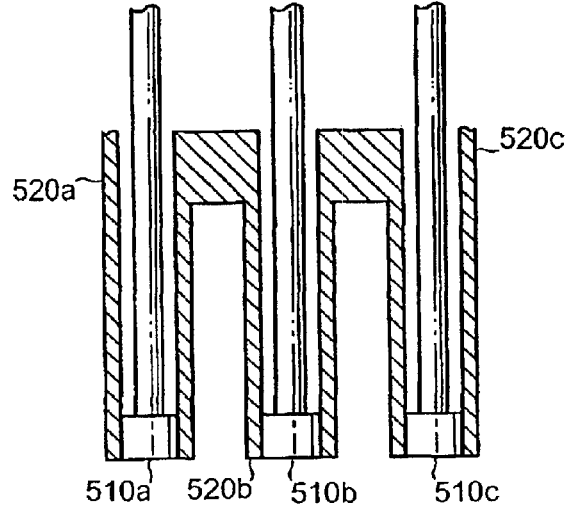
FIG. 6a shows a multi-dose system in accord with the present invention.

FIG. 6a shows an example of a multi-dosing system. The system comprises dosator pistons 510a, 510b, 510c located in tubes 520a, 520b and 520c which are joined together at their upper portions.

The compaction and filling stages take place in the multi-dose system as shown in FIGS. 1b to 1d for a single dosing system. The tubes 520a, 520b and 520c and dosator pistons 510a, 510b, 510c are lowered into the powder reservoir to compact individual areas of powder. The dosator pistons 510a, 510b, 510c are then retracted up the tubes 520a, 520b and 520c to create a cavity in each tube 520a, 520b and 520c and the system is then lowered further into the powder to fill the cavity with compacted powder.

Alternatively, multiple compaction pins may be used to compact the powder and may then either be assembled into the tubes to create a cavity for filling with powder as shown in FIGS. 5a, 5b and 5c or may be replaced by dosator pistons located within the tubes.

Figure 6B:
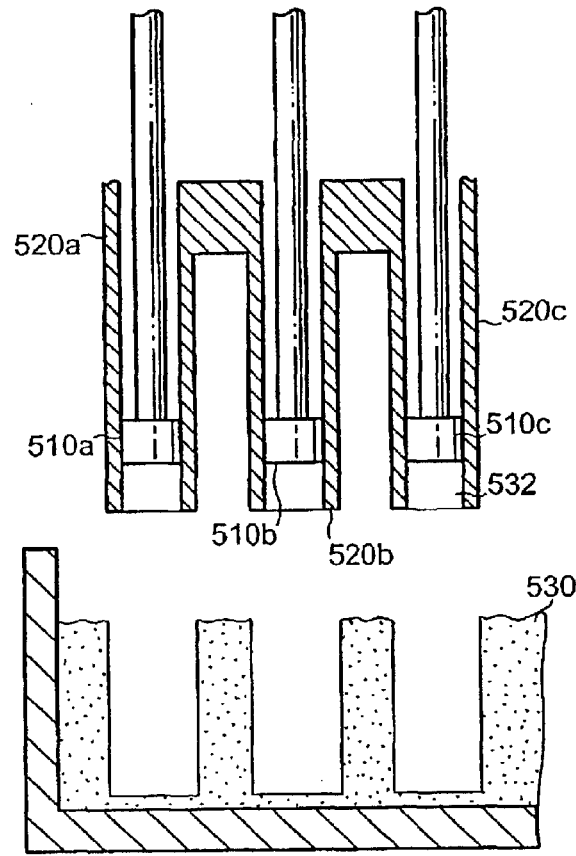
FIGS. 6b and 6c shows the transfer stages subsequent to FIG. 6a in accord with the present invention.

The filled tubes 520a, 520b, 520c are shown in FIG. 6b when they have been raised out of the powder reservoir 530. Seals may be applied to the ends of the tubes 520a, 520b, 520c at this stage to retain the powder in the tubes 520a, 520b, 520c. The tubes 520a, 520b, 520c may then be assembled into a drug delivery system, such as an inhalation device (not shown).

Figure 6C:
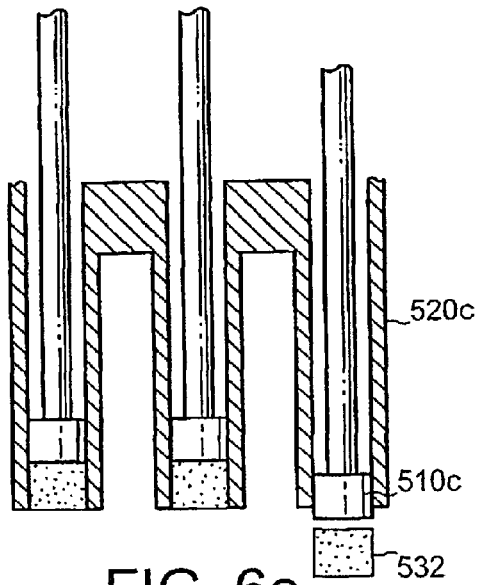

When a dose 532 of powder is required, the dosator piston 510a, 510b, 510c may be used to eject the defined quantity or volume 532 of powder 530 into the inhalation device for inhalation by the patient (FIG. 6c).

Figure 6D:
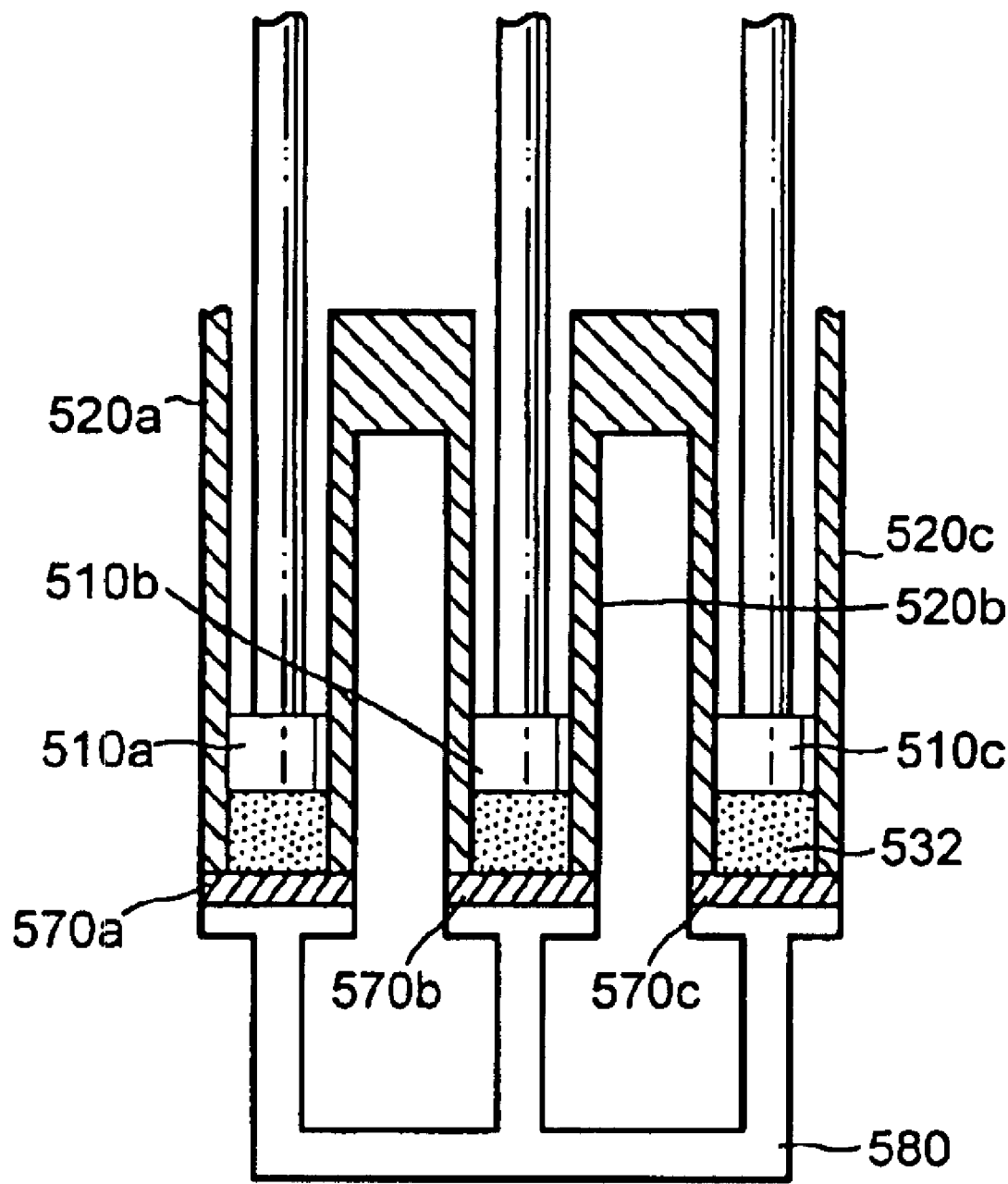
FIG. 6d depicts shows an alternative embodiment wherein the tube is sealed.
Figure 7A:
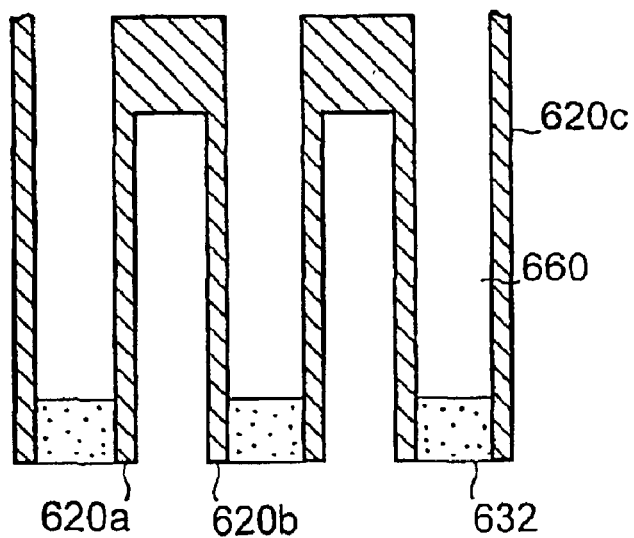
FIGS. 7a and 7b show alternative transfer stages to those shown in FIGS. 6b and 6c in accord with the present invention.
Figure 7B:
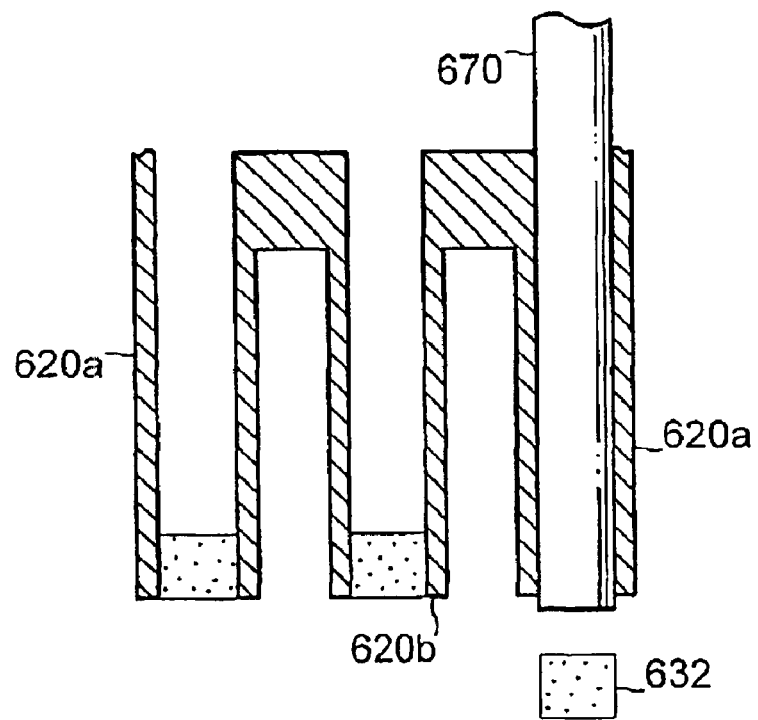

Alternatively, the dosator pistons may be removed from the tubes 620a, 620b, 620c to leave the defined volume of powder 632 occupying a portion of the tubes 620a, 620b, 620c and an empty space 660 in the rest of the tube 620a, 620b, 620c (FIG. 7a). An ejector pin 670 which may form an integral part of the inhalation device (not shown), may be inserted into the empty space 660 in one tube 620c to eject the defined quantity or volume of powder 632 into the inhalation device for inhalation by the patient (FIG. 7b). The ejector pin 670 may be used to pierce any seals 570a. 570b and 570c (as shown in FIG. 6d) applied via seal applier 580 to the tubes 620a, 620b, 620c or a separate piercing device may be used. The tubes 620a, 620b, 620c may be disposed of after the powder dose has been removed.

Figure 8:
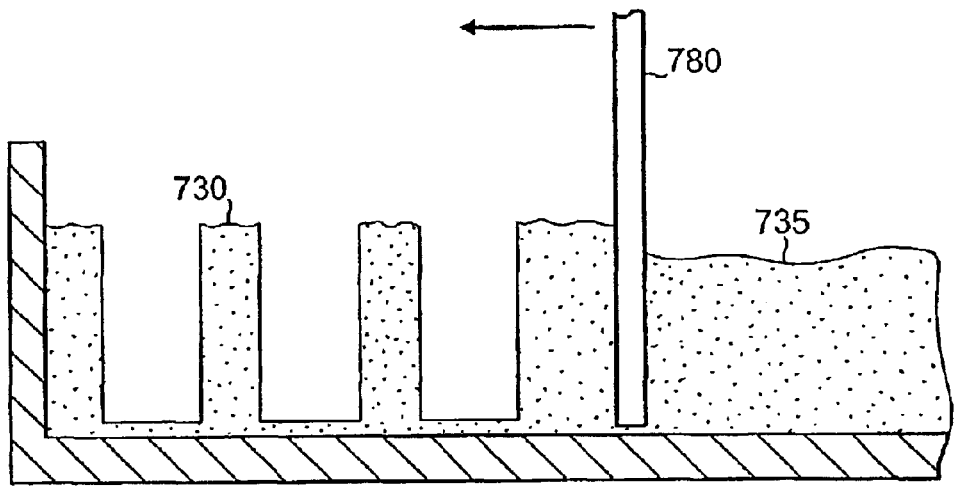
FIG. 8 depicts the action of a disrupter in accord with the present invention.

After removal of the defined volume of powder from the powder reservoir the remaining powder is disrupted using a disrupter so that the holes left following powder removal are filled in (FIG. 8). Suitable means of disrupting the powder reservoir include the use of a disruptor blade 780 or paddle which can be plunged into the powder reservoir 730 and moved throughout it (e.g. in the direction of the arrow in FIG. 8) to leave a more regular bed 735 of powder. In an alternative method, the reservoir of powder is moved relative to the immersed blade or paddle. Another method (not shown) includes plunging a circular or U-shaped wire into the reservoir and moving it (or the reservoir) in a rotational or longitudinal direction to disrupt the powder.

Figure 9:
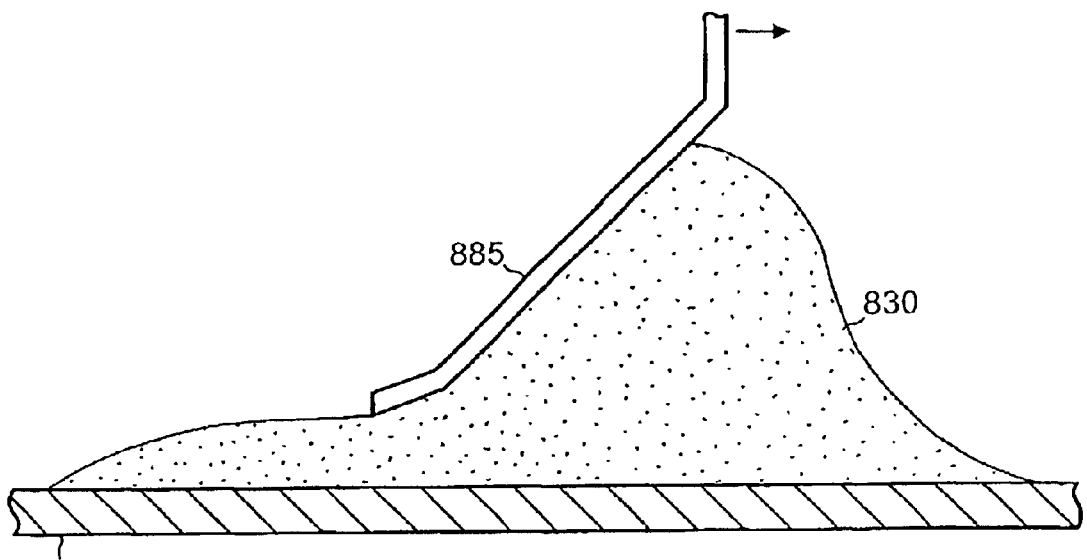
FIG. 9 shows a levelling stage subsequent to the transfer stages in accord with the present invention.

The disrupted bed is then levelled using a leveller blade or other suitable leveller. A leveller blade 885 is shown in FIG. 9. The blade 885 is shown mounted at an angle of approximately 45° to the bottom of the powder bed 838 and depicts one possible configuration of the blade 885 in accord with the present invention. It should however be appreciated that the leveller blade 885 may be mounted at any angle within a wide range, typically (but not exclusively) at an acute angle and preferably between 1 and 60°, and may be varied according to the properties of the powder 830 to optimise powder levelling. When the blade is angled at an acute angle it exerts a compressive force on the powder which produces a powder bed with a more uniform density than using a perpendicular blade. However, it is also possible to use blades that are perpendicular or mounted at an obtuse angle. It should be appreciated that curved or articulated blades may alternatively be used. The tail sections of the leveller blade are not essential to the blade's action although they may also be angled and exert a further compressive force on the powder.

The invention is suitable for filling blister packs or other suitable containers with powdered medicament, particularly for the treatment of respiratory disorders. The invention is also suitable for filling tubes with powdered medicament for the treatment of respiratory disorders to be used in a drug delivery system (e.g. an inhalation device).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate); $\alpha_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It may be appreciated that any of the parts of the apparatus that contact the powder may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims or may include, by way of example and without limitation, one or more of the following claims:

What is claimed is:

1. A method of transferring a defined quantity of powder comprising:
   a) compacting, within a bed of powder, a target area without compacting the entirety of the bed of powder surrounding the target area of powder;
   b) dipping a tube into said compacted target area of powder to fill said tube with a defined volume of powder; and
   c) transferring said defined volume of powder from said tube.

2. A method according to claim 1 wherein the powder is compacted to between 10 and 99% of its original density.

3. A method according to claim 2 wherein the powder is compacted to between 20 and 50% of its original density.

4. A method according to claim 1 wherein the compaction is achievable by the use of a compaction pin.

5. A method according to claim 1 wherein the compaction is achievable by the use of a compaction plate.

6. A method according to claim 1 wherein the compaction is achievable by the use of a dosator piston located within the tube such that at least a portion of said dosator piston is essentially flush with or protrudes from the dipping end of the tube.

7. A method according to claim 1 wherein the compaction is achievable by the use of a dosator piston located within the tube such that at least a portion of said dosator piston is essentially flush with the dipping end of the tube.

8. A method according to claim 6 wherein said dosator piston is slidably retractable within the tube following compaction to create a cavity for filling with the defined volume of powder.

9. A method according to claim 1 wherein the tube is tapered towards its dipping end.

10. A method according to claim 1, wherein said tube has an inner cross sectional area, and wherein the target area of powder is greater than the inner cross sectional area of the tube.

11. A method according to claim 1 wherein, wherein said tube has an inner cross sectional area, and the target area of powder is equal to the inner cross sectional area of the tube.

12. A method according to claim 1 further comprising compacting the powder in the tube subsequent to filling the tube with the defined volume of powder.

13. A method according to claim 6 wherein the defined volume of powder is transferable from the tube by slidable movement of the dosator piston to eject the powder.

14. A method according to claim 1 additionally comprising transferring the powder to a container.

15. A method according to claim 14 wherein the container is selected from the group consisting of a blister pocket, an injection moulded plastic pocket and a capsule.

16. A method according to claim 1 additionally comprising applying a seal to each end of the filled tube, subsequent to dipping the tube into the compacted target area of powder.

17. A method according to claim 16 additionally comprising placing said sealed tube in a drug delivery system.

18. A method according to claim 16 additionally comprising piercing said seal immediately prior to transferring the defined volume of powder.

19. A method according to claim 18 wherein the piercing is achievable by the use of a piercing pin.

20. A method according to claim 17 wherein said piercing pin forms an integral part of said drug delivery system.

21. A method according to claim 16 wherein the defined volume of powder is transferable from said tube by use of a transferring pin to eject the powder into a drug delivery system.

22. A method according to claim 21 wherein said transferring pin forms an integral part of the drug delivery system.

23. A method according to claim 19 wherein the piercing pin and the transferring pin are identical.

24. A method according to claim 1 additionally comprising levelling the powder prior to compaction.

25. A method according to claim 24, wherein the levelling is achieved by the use of a leveller blade movable on a linear sweeping path.

26. A method according to claim 25 wherein said leveller blade is perpendicular to said linear sweeping path.

27. A method according to claim 25 wherein the leveller blade presents a forward acute angle to the linear sweeping path.

28. A method according to claim 27 wherein said forward acute angle is between 40 and 50°.

29. A method according to claim 1 additionally comprising disrupting the powder following removal of the defined quantity of powder.

30. A method according to claim 1 wherein the powder comprises a medicament.

31. A method according to claim 30 wherein the medicament is selected from the group consisting of albuterol, salmeterol, fluticasone propionate and beclomethasone dipropionate and salts or solvates thereof and any mixtures thereof.

32. A method according to claim 31 wherein said mixture comprises salmeterol xinafoate and fluticasone propionate.

33. A method according to claim 30 wherein the powder further comprises an excipient.

34. A method according to claim 33 wherein the excipient is a sugar.

35. A method according to claim 1 wherein the powder is selected from the group consisting of an explosive powder, a sweetener, herbal product, food supplement and vitamin.

36. An apparatus for transferring a defined quantity of powder which comprises;
   a) a powder reservoir containing a bulk of powder;
   b) a tube suitable for containing a defined volume of powder, said tube having a dipping end;
   c) a compactor for compacting a target area of powder within said bulk of powder, without compacting substantially all of the bulk of powder surrounding the target area of powder; wherein said compacted powder from said target area is positionable within said tube to form a filled tube; and
   d) a transferor to transfer said defined volume of powder from said tube.

37. An apparatus according to claim 36 wherein the compactor comprises a compaction pin.

38. An apparatus according to claim 36 wherein the compactor comprises a compaction plate.

39. An apparatus according to claim 36 wherein the compactor comprises a dosator piston located within the tube such that at least a portion of said dosator piston is essentially flush with or protrudes from the dipping end.

40. An apparatus according to claim 36 wherein the compactor comprises a dosator piston located within the tube such that at least a portion of said dosator piston is essentially flush with the dipping end.

41. An apparatus according to claim 39 wherein said dosator piston is slidably retractable within the tube to create a cavity for filling with the defined volume of powder.

42. An apparatus according to claim 36 wherein the tube is tapered towards said dipping end.

43. An apparatus according to claim 36, wherein said tube has an inner cross sectional area, wherein the target area of powder is greater than the inner cross sectional area of the tube.

44. An apparatus according to claim 36, wherein said tube has an inner cross sectional area, wherein the target area of powder is equal to the inner cross sectional area of the tube.

45. An apparatus according to claim 36 additionally comprising a seal applier to apply a seal to each end of the filled tube to form a sealed tube, subsequent to dipping the tube into the compacted target area of powder.

46. An apparatus according to claim 45 additionally comprising a piercer to pierce said seal immediately prior to transferring the defined volume of powder.

47. An apparatus according to claim 46 wherein the piercer comprises a piercing pin.

48. An apparatus according to claim 47 wherein said piercing pin forms an integral part of a drug delivery system.

49. An apparatus according to claim 36 wherein the transferor comprises a transferring pin.

50. An apparatus according to claim 49 wherein said transferring pin forms an integral part of a drug delivery system.

51. An apparatus according to claim 47 wherein the transferor and piercing pin are identical.

52. An apparatus according to claim 36 wherein the transferor transfers the defined volume of powder to a container.

53. An apparatus according to claim 52 wherein the container is selected from the group consisting of a blister pocket, an injection moulded plastic pocket and a capsule.

54. An apparatus according to claim 52 wherein the transferor comprises the dosator piston which slidably moves within the tube to eject the powder.

55. An apparatus according to claim 36 additionally comprising a leveller to level the powder prior to compaction.

56. A method according to claim 55, wherein the levelling is achieved by the use of a leveller blade movable on a linear sweeping path.

57. A method according to claim 56 wherein said leveller blade is perpendicular to said linear sweeping path.

58. A method according to claim 57 wherein the leveller blade presents a forward acute angle to the linear sweeping path.

59. A method according to claim 58 wherein the forward acute angle is between 40° and 50°.

60. An apparatus according to claim 36 additionally comprising a disrupter to disrupt the powder following removal of the defined quantity of powder.

61. An apparatus according to claim 36 wherein the powder comprises a medicament.

62. An apparatus according to claim 61 wherein the medicament is selected from the group consisting of albuterol, salmeterol, fluticasone propionate and beclomethasone dipropionate and salts or solvates thereof and any mixtures thereof.

63. An apparatus according to claim 62 wherein said mixture comprises salmeterol xinafoate and fluticasone propionate.

64. An apparatus according to claim 61 wherein the powder further comprises an excipient.

65. An apparatus according to claim 64 wherein the excipient is a sugar.

66. An apparatus according to claim 45 wherein the powder is selected from the group consisting of an explosive powder, a sweetener, a herbal product, powdered food supplement and vitamins.

67. A transferred powder sample obtainable by the method according to claim 1.

* * * * *